United States Patent [19]

Sorenson et al.

[11] Patent Number: 5,207,752
[45] Date of Patent: May 4, 1993

[54] IONTOPHORETIC DRUG DELIVERY SYSTEM WITH TWO-STAGE DELIVERY PROFILE

[75] Inventors: Paul D. Sorenson, Blaine; John D. Badzinski, Coon Rapids; Gary A. Lattin, Forest Lake; Larry A. McNichols, Coon Rapids, all of Minn.

[73] Assignee: Alza Corporation, Palo Alto, Calif.

[21] Appl. No.: 671,306

[22] Filed: Mar. 21, 1991

Related U.S. Application Data

[63] Continuation-in-part of Ser. No. 502,176, Mar. 30, 1990, abandoned.

[51] Int. Cl.$^5$ ............................................. A61N 1/30
[52] U.S. Cl. ..................................................... 604/20
[58] Field of Search ............... 604/20, 21; 128/419 R, 128/803

[56] References Cited

U.S. PATENT DOCUMENTS

| | | |
|---|---|---|
| 3,163,166 | 12/1964 | Brant et al. |
| 3,618,601 | 11/1971 | Richardson |
| 3,677,268 | 7/1972 | Reeves |
| 3,794,910 | 2/1974 | Ninke et al. |
| 3,955,583 | 5/1976 | Horauf |
| 4,141,359 | 2/1979 | Jacobsen et al. |
| 4,149,533 | 4/1979 | Ishikawa et al. |
| 4,177,817 | 12/1979 | Bevilacqua |
| 4,209,020 | 6/1980 | Nielsen |
| 4,211,222 | 7/1980 | Tapper |
| 4,215,696 | 8/1980 | Bremer et al. |
| 4,292,968 | 10/1981 | Ellis |
| 4,301,794 | 11/1981 | Tapper |
| 4,325,367 | 4/1982 | Tapper |
| 4,340,047 | 7/1982 | Tapper et al. |
| 4,450,844 | 5/1984 | Quisno |
| 4,474,570 | 10/1984 | Ariura et al. |
| 4,557,723 | 12/1985 | Sibalis |
| 4,619,252 | 10/1986 | Ibbott |
| 4,622,031 | 11/1986 | Sibalis |
| 4,640,689 | 2/1987 | Sibalis |
| 4,698,062 | 10/1987 | Gale et al. |
| 4,708,716 | 11/1987 | Sibalis |
| 4,731,049 | 3/1988 | Parsi |
| 4,731,926 | 3/1988 | Sibalis |
| 4,808,152 | 2/1989 | Sibalis |
| 4,822,334 | 4/1989 | Tapper |
| 4,851,229 | 7/1989 | Magruder et al. |
| 4,865,582 | 9/1989 | Sibalis |
| 4,883,457 | 11/1989 | Sibalis |

FOREIGN PATENT DOCUMENTS

| | | |
|---|---|---|
| 0079405 | 5/1983 | European Pat. Off. |
| 0254965 | 2/1988 | European Pat. Off. |
| 8808729 | 11/1988 | PCT Int'l Appl. |

*Primary Examiner*—Lee S. Cohen
*Attorney, Agent, or Firm*—Merchant, Gould, Smith, Edell, Welter & Schmidt

[57] ABSTRACT

A two-stage iontophoretic drug delivery system provides that iontophoretic current is delivered at a first level for a first predetermined interval to rapidly introduce a therapeutic agent into the bloodstream and thereafter reduced to a second lower level to maintain a desired steady-state therapeutic level of the agent. One embodiment provides that the initial interval is maintained sufficiently long to provide a peak dosage, thereafter which the current is shut off to allow concentration of the agent to subside in the bloodstream, whereupon a maintenance level of iontophoretic current is initiated. Another embodiment provides that the patient may selectively initiate a brief interval of increased iontophoretic current level to attain a brief interval of increased dosage.

22 Claims, 5 Drawing Sheets

IONTOPHORETIC DRUG DELIVERY SYSTEM WITH TWO-STAGE DELIVERY PROFILE

CROSS-REFERENCE TO RELATED APPLICATION

This application is a continuation-in-part of U.S. patent application Ser. No. 07/502,176, filed Mar. 30, 1990, now abandoned.

TECHNICAL FIELD OF THE INVENTION

The present invention pertains generally to the field of medicine, and more particularly to an iontophoretic device for introducing ionic substances into a body.

BACKGROUND OF THE INVENTION

Iontophoresis is a method for introducing ionic substances into a body. The method utilizes direct electrical current to drive the ionized substances, such as drugs, through the intact skin or other body surface. This has proven to be very useful in numerous medical applications. U.S. Pat. Nos. 3,991,755 issued to Jack A. Vernon, et al and 4,141,359 issued to Stephen C. Jacobsen, et al disclose examples of iontophoretic devices and some applications of the devices. The iontophoretic process has been found to be useful in the administration of lidocaine hydrochloride, hydrocortisone derivatives, acetic acid, fluoride, penicillin, dexamethasone sodium phosphate and many other drugs.

In iontophoretic devices two electrodes are used. One electrode, called the active electrode, is the electrode at which the ionic substance is driven into the body. The other electrode, called the indifferent or ground electrode, serves to close the electrical circuit through the body. It will be appreciated by those skilled in the art that the active electrode must hold, contain or otherwise have available to it a source of the ionic substance. Thus, in the prior art the active electrode is generally relatively complex compared to the indifferent electrode.

Generally, prior iontophoretic drug delivery systems provide a single drug delivery rate. Such rate is obtained by applying a constant iontophoretic current designed to achieve a certain steady-state therapeutic concentration of drug in the body. With the use of such systems, there is a certain delay between the time that the iontophoretic maintenance current is initiated and when the desired therapeutic level of concentration is reached. Such delay may be, for example, thirty minutes from the time the iontophoretic current is initiated. In many cases, however, it is desirable or necessary that the iontophoretic drug reach therapeutic levels relatively fast. For example, where iontophoresis is used to deliver a narcotic pain killer, the patient often cannot tolerate a delay of even fifteen minutes. If the iontophoretic drive current is initially set at a relatively high level in order to encourage the rapid migration of iontophoretic drug into the bloodstream, the system will ultimately reach a steady-state level higher than desired or therapeutically safe. As a result, there is a need for an iontophoretic delivery system wherein therapeutic levels of drug concentration in the blood can be rapidly obtained while at the same time achieving a desirable steady-state maintenance level of administration.

SUMMARY OF THE INVENTION

The present invention provides method and apparatus for iontophoretic drug delivery wherein there is initially provided a high current level for a predetermined time to quickly drive the iontophoretic drug into the body to reach the therapeutic level, after which the current is automatically reduced to achieve a steady-state administration of the drug at a maintenance level. This scheme allows rapid input of drug to the bloodstream while minimizing overshoot above the maximum desirable level of the therapeutic dose window for the drug.

The present invention further provides method and apparatus for iontophoretic drug delivery wherein the initial high current level is maintained for a predetermined time to provide that drug concentration in the bloodstream reaches a temporary peak value and thereafter subsides to a maintenance level. For this purpose, the invention contemplates applying the initial current until a time $T_1$, shutting off current delivery for a delay period until time $T_2$, and then initiating a current level sufficient to maintain the drug at a maintenance concentration level.

The invention further contemplates, during operation in a maintenance mode, temporarily stepping up the applied current to provide a temporary increase in drug dosage. Apparatus for this purpose is provided and includes a user-activatable timer, which is used to control the time during which the increased current is applied.

The invention further contemplates various apparatus for programming the current delivery characteristics of the iontophoretic devices according to the present invention.

DETAILED DESCRIPTION OF THE INVENTION

Figure 1:
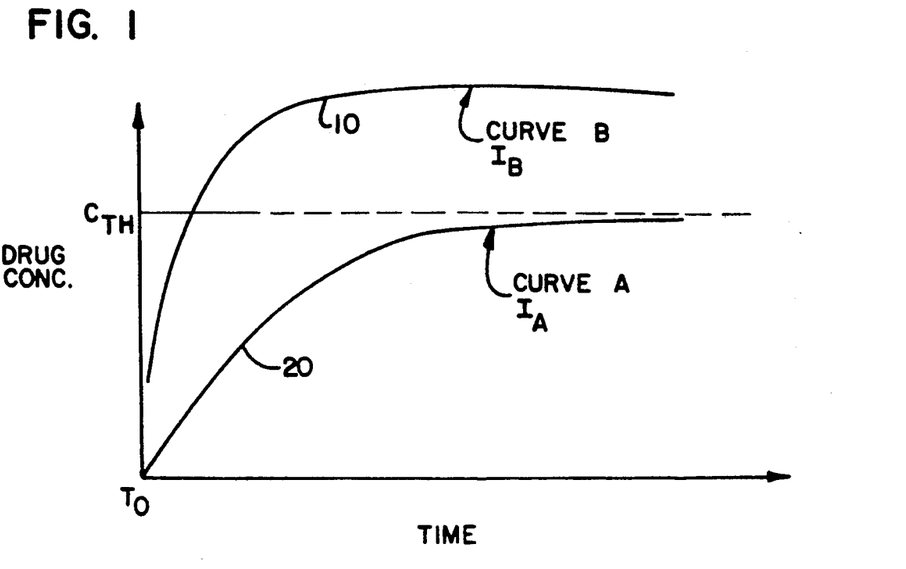
FIG. 1 is a plot of the drug concentration vs. time for two different iontophoretic current levels.

Referring now to FIG. 1, there is shown a plot of drug concentration vs. time, wherein drug concentration is represented on the y axis and time is represented on the x axis. A first curve 10 in FIG. 1 represents a plot of the level of drug concentration (in the body) vs. time, beginning from time 0, utilizing an iontophoretic current $I_B$ of a certain magnitude. Curve 20 represents the drug concentration profile over time for an iontophoretic current $I_A$, of a lesser magnitude than $I_B$. As illustrated, utilizing current level $I_B$, the level of concentration in the bloodstream reaches a desired level $C_{th}$ (the desired systemic therapeutic level of drug) at a time substantially earlier than that achieved using the current $I_A$. As also indicated, the steady-state concentration level for current $I_B$ is greater than that for current $I_A$. Thus, while current $I_B$ will cause the iontophoretic drug to reach therapeutic levels in the bloodstream faster than that of $I_A$, it also attains a higher steady-state concentration level. FIG. 1 thus demonstrates that when using a single current magnitude one can either achieve rapid introduction or a desired steady-state level, but not both.

Figure 2:
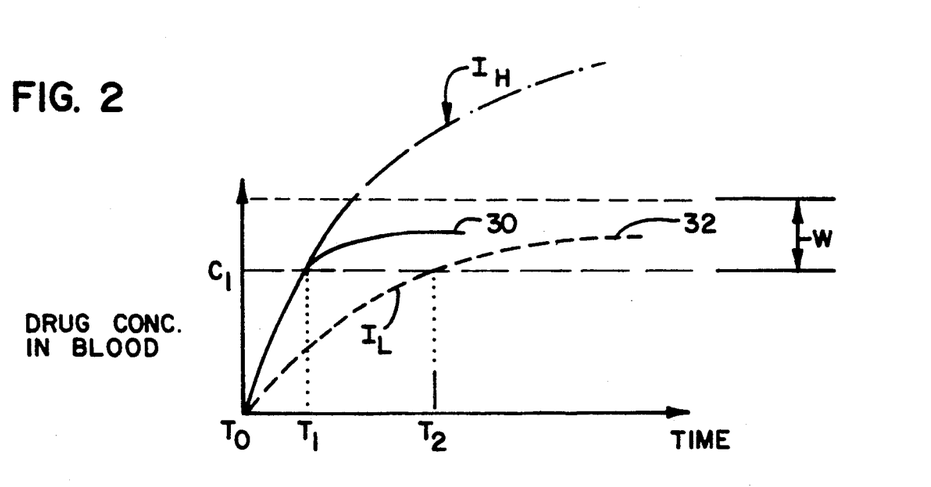
FIG. 2 is a drug concentration vs. time plot illustrating a two-stage delivery system according to present invention.

Referring now to FIG. 2, there is shown a drug concentration versus time plot illustrating a two-stage delivery system according to present invention. Preferably, the present invention provides that a first level of current $I_H$ be used to drive the iontophoretic drug solution into the bloodstream at a rapid rate. Subsequently, in the second stage of delivery, the iontophoretic current is reduced to $I_L$, to attain the desired steady-state therapeutic level concentration within a therapeutic window W. As shown in FIG. 2, the present invention contemplates a first stage of drug delivery utilizing a current level $I_H$ until the time $T_1$, at which point $I_H$ is stepped down to level $I_L$. As shown in FIG. 2, the result is a drug delivery profile 30 wherein the drug reaches a certain concentration $C_1$ by the time $T_1$, and thereafter maintains substantially the same level of concentration in the bloodstream. For contrast, dotted line profile 32 represents the drug delivery profile attained where current level $I_L$ is used alone from initialization.

Figure 3:
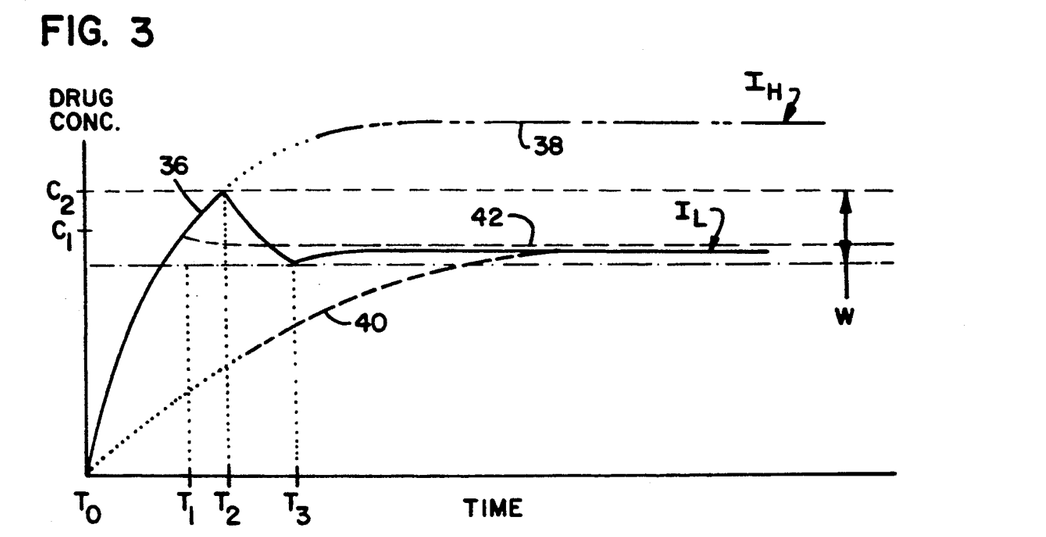
FIG. 3 is a drug concentration vs. time plot illustrating yet another method of two-stage delivery according to present invention wherein there is provided a delay between the first and second stages of delivery.

Alternatively, as illustrated with respect to plot 36 in FIG. 3, the present invention provides that the initial iontophoretic current level $I_H$ may be maintained for a longer period of time, for example until the time $T_2$, to achieve a higher initial concentration level $C_2$ in the bloodstream than is desireable for steady-state. This approach may be desirable, for instance, where an initial high dose of a painkiller is sought, with subsequent reduction to a lower maintenance level. At the time $T_2$, the iontophoretic current is turned off until a time $T_3$ to allow the initial concentration to reduce to the lower maintenance level. At time $T_3$, the current $I_L$ is initiated to maintain the concentration level at the desired steady-state level $C_1$ within the therapeutic window W. For comparison sake, dashed line 38 represents the steady-state concentration level for current $I_H$; dashed line 42 represents the drug concentration profile attained if current $I_L$ is applied beginning at the time $T_1$ (in a manner similar to that described above with reference to FIG. 2); and dashed line 40 represents the concentration profile wherein $I_L$ is used alone from initialization.

Figure 4:
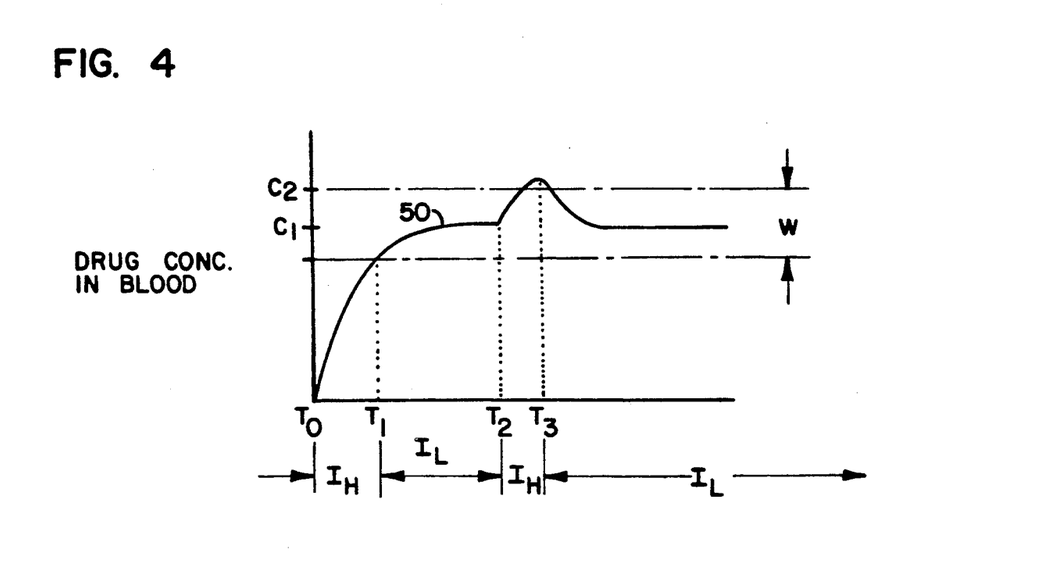
FIG. 4 is a drug concentration vs. time plot illustrating the method according to present invention wherein the iontophoretic current level is temporarily increased from a steady-state level.

FIG. 4 illustrates yet another alternative embodiment of the present invention. Concentration profile 50 is attained by applying a current $I_H$ until a time $T_1$, and then a current $I_L$ to a time $T_2$. From time $T_2$ to $T_3$, the current is increased back to the level $I_H$, or some other level higher than $I_L$, to achieve a temporary dosage increase up to a concentration level $C_2$. The invention contemplates that the temporary increase in dosage be under user control, as would be desirable in the case of a patient receiving an iontophoretically administered narcotic. The system would thus allow the patient to temporarily increase the narcotic dosage to alleviate pain in peak periods, after which the dosage would automatically return to a maintenance level.

Figure 5:
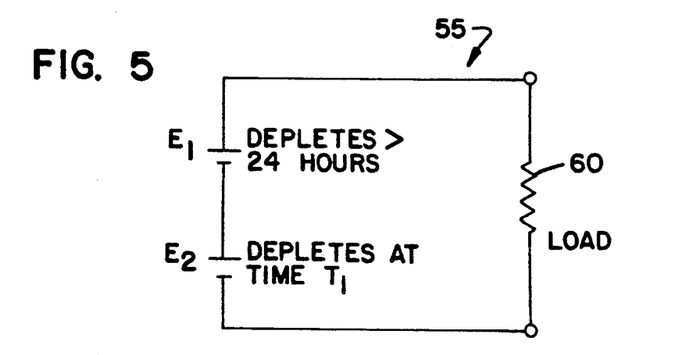
FIGS. 5 and FIGS. 6 illustrate two alternative embodiments of the two-stage delivery apparatus according to present invention.
Figure 6:
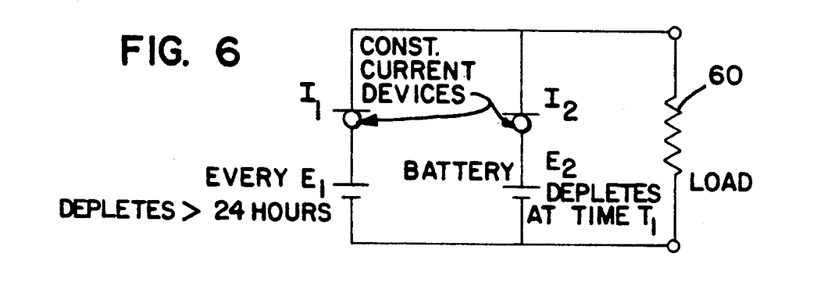

Referring now to FIGS. 5 and 6, there are shown two simplified circuits for the attainment of the two-stage delivery system according to the present invention. In FIG. 5 a circuit 55 has a pair of batteries $E_1$ and $E_2$. The tissue is represented in the schematic by resistive element 60. To attain the two-stage delivery profile, a first battery $E_2$ can be provided which will deplete its energy supply at the time $T_1$, with the battery $E_1$ continuing to produce energy for iontophoretic current for a longer period, for example, 24 hours. This circuit thus allows that the iontophoretic current be supplied at a rate proportional to the voltage $E_1$ and $E_2$ until a time $T_1$, and then at a rate proportional to the voltage $E_1$ for the duration. In FIG. 6, there is shown an alternative design of generally the same construction, with batteries E1 and E2 configured in parallel and with the inclusion of constant current devices in series therewith respectively. Again, battery $E_2$ would be designed to deplete itself after a time $T_1$, with $E_2$ continuing to supply power for a longer interval.

Figure 7:
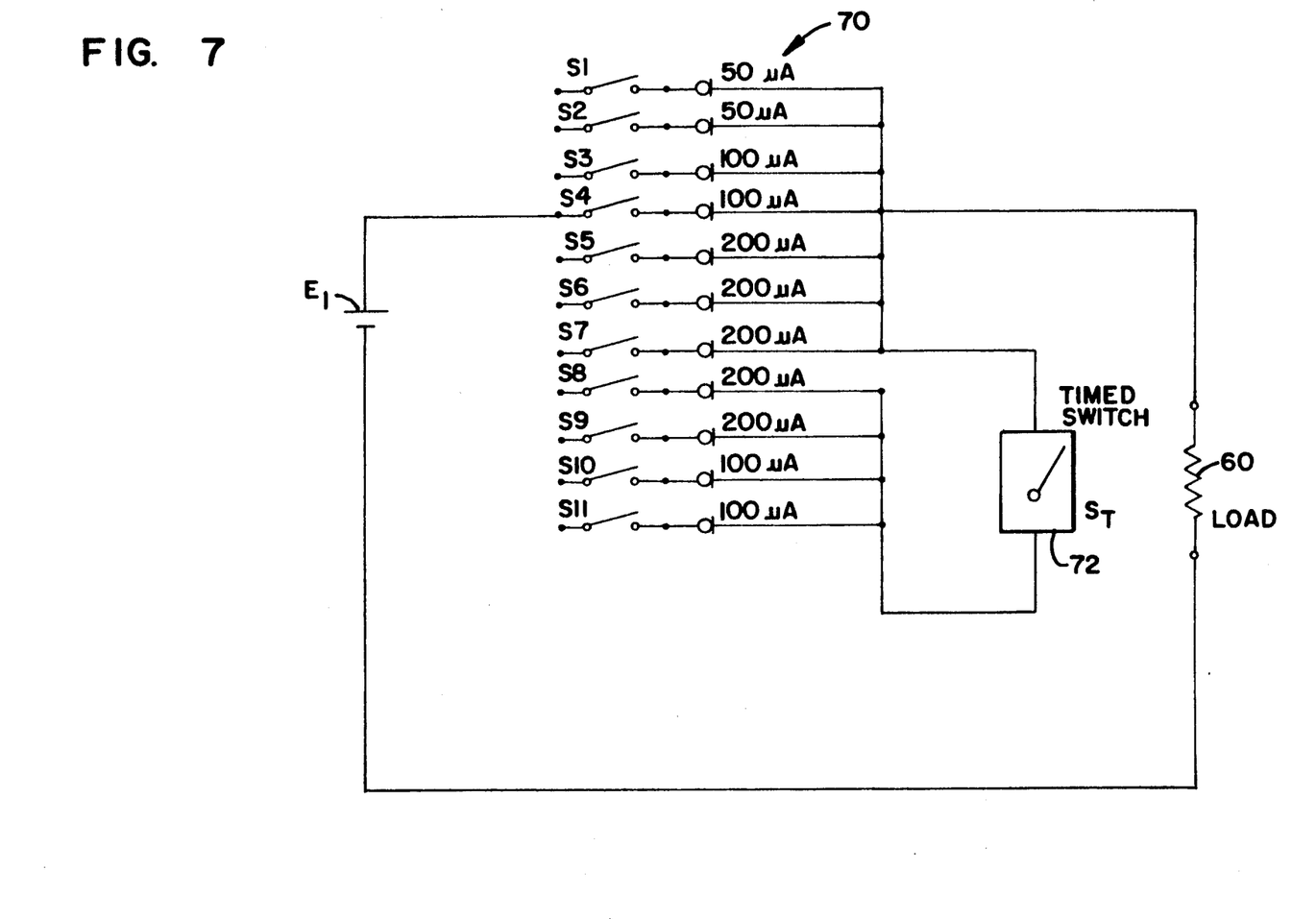
FIG. 7 illustrates a programmable two-stage delivery system according to present invention.

Referring now to FIG. 7 there is shown a programmable circuit for achieving the two-stage delivery system according to present invention. The device of FIG. 7 includes a battery $E_1$ switched through a plurality of constant current diodes 70. Switches $S_1$-$S_7$ switch battery $E_1$ through the respective constant current diodes of varying current settings associated therewith to the body tissue 60. Switches $S_8$-$S_{11}$ switch $E_1$ through their associated constant current diodes and timed switch 72 to tissue 60. Switches $S_1$-$S_7$ may be selectively closed or fused to provide the desired current $I_L$, as per example illustrated in FIG. 2. For example, if $I_L$ was to be equal to 200 microamps, switches $S_3$ and $S_4$ can be fused closed. The current level $I_H$ is provided by selectively fusing or switching closed any one or a combination of switches $S_8$-$S_{11}$. For instances, with $I_L$ equal to 200 microamps the level $I_H$ of 400 microamps would be provided by fusing switch $S_8$ shut. Thus, during the time that switch 72 is closed, from the time $T_0$ to $T_1$ as illustrated in FIG. 2, a current level of 400 microamps would be provided to tissue 60. When timed switch 72 opens at time $T_1$, the current level would be reduced to 200 microamps.

Figure 8:
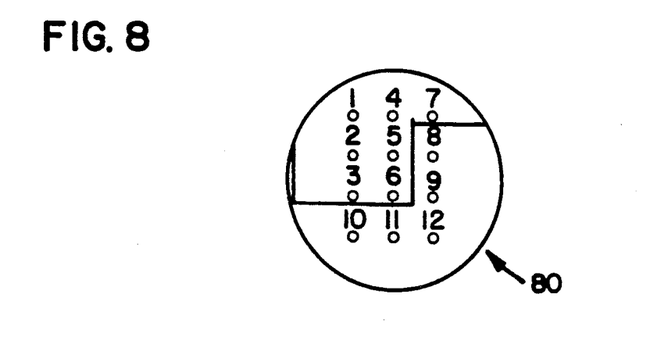
FIG. 8 is an illustration of a programming mechanism for programming the device of FIG. 7 according to present invention.

Referring now to FIG. 8, there is shown a plan view of one possible mechanism 84 for programming switches $S_1$ through $S_{11}$. Mechanism 80 includes a plurality of holes, each associated with a particular switch,: The switches may be fused or closed by punching a stiletto into the holes. For example if it was desired to fuse switches $S_1$ and $S_2$, the stiletto would be punched into holes 1 and 2 on mechanism 80. Similarly, any combination of switches $S_1$ through $S_{11}$ could be attained by punching the corresponding holes of mechanism 80.

Alternatively, the switching of $S_1$ through $S_{11}$ could be obtained through UV light programming or by pulsed electrical energy to make or break fusible contacts. Photo-diodes or other photo-optic devices could also be used in place of switches $S_1$ through $S_{11}$ and their corresponding diodes. Such devices could be programmed by applying selected wavelengths of light thereto so that various wavelengths of light would set desired levels of current.

Figure 9:
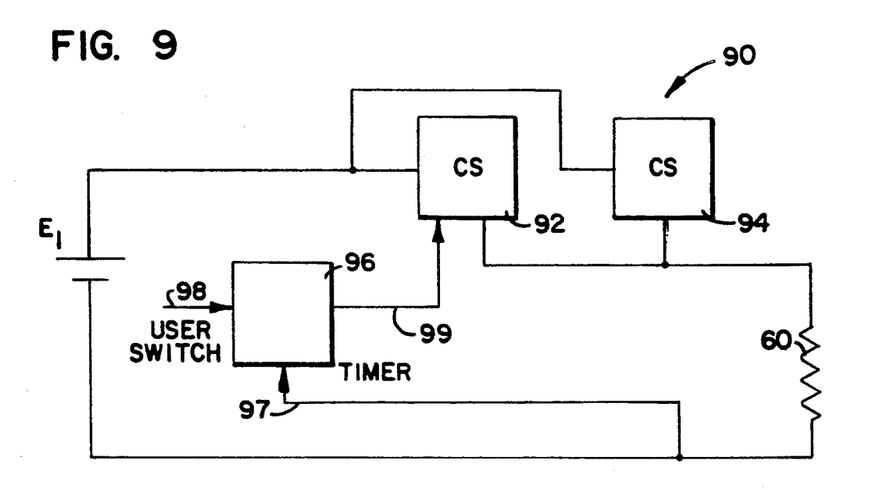
FIG. 9 is an alternate embodiment of a two-stage delivery system according to present invention.

Referring now to FIG. 9, there is shown yet another possible alternative embodiment of an iontophoretic current delivery device according to present invention. Device 90 includes battery $E_1$, first and second current sources 92 and 94 and a timer 96. In operation, current source 94 controls the current level $I_L$ as discussed, for example, with respect to FIG. 2. Current source 92 provides an incremental current source which, when added to $I_L$, provides the current level $I_H$. In operation, timer 96 has a first input 97 which detects the flow of current through load 60 and in turn produces an output signal 99 to current source 92 for a predetermined interval of time, for example ten minutes. Output signal 99 activates current source 92 for the predetermined interval in order to provide that the higher current level $I_H$ be applied to load 60 during the interval, for example, ten minutes (i.e. to a time $T_1$). After the predetermined interval, timer 96 deactivates the signal on line 99, thereby removing current source 92 from the circuit, whereupon current level returns to the level $I_L$. Timer 96 can also be configured with a user activatable switch input 98, whereby it can be activated selectively by the user, to time-out another predetermined interval and thereby increase the current level in load 60 to the level $I_H$ during the interval. This system thus provides the method of delivery explained with respect to FIG. 4. When configured with a user-activatable switch 98, timer 96 includes a circuit for preventing activation of the timer via switch 98 for a predetermined interval following each activation by the user. Accordingly, the user is permitted to increase the iontophoretic current level, and thereby the level of dose of iontophoretic drug in the patient's bloodstream, only once per a given period of time. For example, timer 96 may be programmed to respond to a user activation only once every hour. In addition, timer 96 preferably includes a counter which will permit the user to activate a higher dose only a predetermined number of times over a given interval. For instance, it may be desirable to limit the number of increased doses within a twelve-hour period to six.

Figure 10:
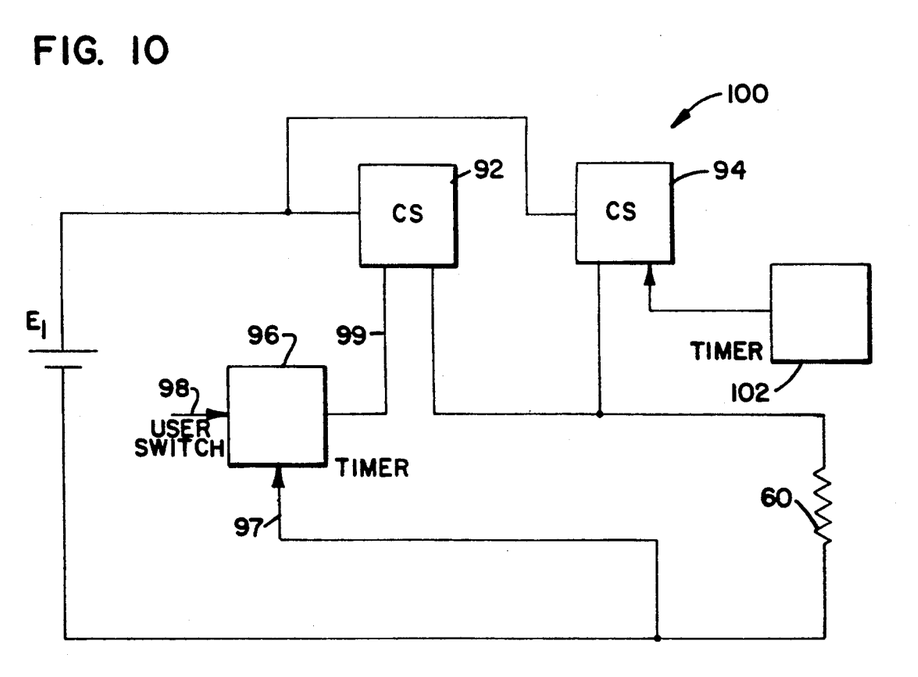
FIG. 10 is a schematic illustration of a two-stage delivery system according to present invention wherein there is provided means for temporarily increasing the level of current and drug concentration or a predetermined interval of a steady-stage level.

Referring now to FIG. 10, there is shown an iontophoretic delivery device which can attain the method of delivery explained above with respect to FIG. 3. Device 100 has generally the same construction as that of device 90 illustrated in FIG. 9, and like reference numbers identify like elements between the two drawings. In device 100, an additional timer 102 is provided to control current source 94. Timer 102 provides that current source 94 may be deactivated for a period of time following an initial interval of current delivery. For example, with reference to FIG. 3, timer 96 may be programmed to activate current source 92 for a period of fifteen minutes following initiation of current delivery. With respect to FIG. 3, this time interval would end at the time $T_2$. At the time $T_2$, timer 102 would deactivate current source 94 for another predetermined interval, for example ten minutes, such that both current sources 92 and 94 would be shut off during this ten minute interval. With respect to FIG. 3, this ten minute interval would end at the time $T_3$. After the ten minute interval, current source 94 would be reactivated to deliver the lower level current $I_L$ associated with the maintenance concentration.

It is contemplated that the various embodiments of the invention may be combined in various combinations to provide, for example, an embodiment combining the effects of the system described with respect to FIG. 3 and that described with respect to FIG. 4, or a combination of the various devices described in the drawings.

Although the invention has been described with specific reference to iontophoretic drug delivery, it is generally applicable to any "electrotransport" system for transdermal delivery of therapeutic agents, whether charged or uncharged. As understood in the art, when the therapeutic agent is charged, the process is referred to as iontophoresis. When the therapeutic agent delivered is uncharged, delivery may be accomplished by means known as electroosmosis. Electroosmosis is the transdermal flux of a liquid solvent (e.g., the liquid solvent containing the uncharged drug or agent) which is induced by the presence of an electric field imposed across the skin by the active electrode. Therefore, the terms "iontophoresis" and "iontophoretic" used herein refer to either the delivery of charged drugs or agents, the delivery of uncharged drugs or agents by the process of electroosmosis (also referred to as electrohydrokinesis, electro-convention or electrically-induced osmosis) or both.

The expressions "drug" and "therapeutic agent" are used interchangeably herein and are intended to have their broadest interpretation as they include any therapeutically active substance which is delivered to a living organism to produce a desired, usually beneficial, effect. In general, this includes therapeutic agents in all of the major therapeutic areas including, but not limited to, anti-infectives such as antibiotics and antiviral agents, analgesics and analgesic combinations, anesthetics, anorexics, antiarthritics, antiasthmatic agents, anticonvulsants, antidepressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary, anticholinergics, sympathomimetrics, xanthine derivatives, cardiovascular preparations including calcium channel blockers, beta-blockers, antiarrythmics, antihypertensives, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, proteins, peptides, psychostimulants, sedatives and tranquilizers.

The invention is also useful in the controlled delivery of peptides, polypeptides, proteins and other macromolecules. These macromolecular substances typically have a molecular weight of at least about 300 daltons, and more typically a molecular weight in the range of about 300 to 40,000 daltons. Specific examples of peptides and proteins in this size range include, without limitation, LHRH, LHRH analogs such as buserelin, gonadorelin, naphrelin and leuprolide, GHRH, insulin, heparin, calcitonin, endorphin, TRH, NT-36 (chemical name: N=[[(s)- 4-oxo-2-azetidinyl]carbonyl]-L-histidyl-L-prolinamide), liprecin, pituitary hormones (e.g., HGH, HMG, HCG, desmopressin acetate, etc.), follicle luteoides, aANF, growth factor releasing factor (GFRF), bMSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hyaluronidase, interferon, interleukin-1, interleukin-2, menotropins (urofollitropin (FSH) and LH), oxytocin, streptokinase, tissue plasminogen activator, urokinase, vasopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neurotrophic factors, growth factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 antitrypsin (recombinant).

Although the invention has been described above with respect to its preferred form, those with skill in the art will readily recognize that various modifications and changes may be made thereto without departing from the spirit and scope of the claims appended hereto.

We claim:

1. A method of iontophoretic drug delivery wherein there is provided at least two electrodes carrying or in contact with an ionized therapeutic agent and wherein the electrodes and agent are positioned against body tissue to form an electrical path for an iontophoretic current traveling from one electrode to the other, said method comprising the steps of:
   (a) inducing a first level of iontophoretic current between said electrodes wherein the ionized therapeutic agent is delivered into the tissue at a first rate and maintaining said first level for a predetermined interval so that the agent is rapidly introduced into the tissue; and
   (b) reducing said first level to a second lower level of iontophoretic current at a time when the concentration of therapeutic agent is substantially near that desired for a maintenance level, said lower level of current being sufficient to maintain said desired concentration level.

2. The method of iontophoretic drug delivery according to claim 1 wherein the predetermined interval for maintaining the first level of iontophoretic current is a time sufficient to achieve an initial concentration level higher than the maintenance level and further comprising the steps of:
   shutting off the first level of iontophoretic current for a predetermined delay period following the predetermined interval, the delay period sufficient to allow the initial concentration level to reduce to the maintenance level; and
   including the second level of iontophoretic current after the predetermined delay period to maintain the desired concentration level.

3. The method of iontophoretic drug delivery according to claim 1 further comprising the steps of:
   stepping up the iontophoretic current, for a second predetermined interval, from the maintenance level to a higher level of iontophoretic current for increasing the concentration of the therapeutic agent in the body; and
   reducing the iontophoretic current back to the lower level of iontophoretic current after the second predetermined interval expires for maintaining the desired concentration level.

4. The method of iontophoretic drug delivery according to claim 3 wherein stepping up the iontophoretic current is user controlled.

5. The method of iontophoretic drug delivery according to claim 3 wherein the higher level of iontophoretic current is the first level of iontophoretic current.

6. Apparatus for introducing an ionized therapeutic agent into the body, comprising:
   at least two electrodes;
   iontophoretic current generation means for:
      (i) driving a first level of iontophoretic current through said electrodes and the body tissue said electrodes are attached to, said first level applied for a predetermined interval; and
      (ii) driving a second, lower level of iontophoretic current through said electrodes and the associated body tissue beginning after said predetermined interval, said predetermined interval being timed so that the concentration of therapeutic agent in the body obtains approximately the desired concentration level during the predetermined interval and so that said second current level substantially maintains the desired concentration level thereafter.

7. The apparatus for introducing an ionized therapeutic agent into the body according to claim 6 wherein the predetermined interval for driving the first level of iontophoretic current through the electrodes and the body tissue is a time sufficient to achieve an initial concentration level higher than the desired concentration level; and the iontophoretic current generation means further comprises:
   means for timing a predetermined delay period following the predetermined interval, the delay period sufficient to allow the initial concentration level to reduce to the desired concentration level; and
   means for activating the iontophoretic current generation means for driving the second iontophoretic current after the predetermined delay period to maintain the desired concentration level.

8. The apparatus for introducing an ionized therapeutic agent into the body according to claim 6 wherein the iontophoretic current generation means further comprises:
   means for stepping up the iontophoretic current from the desired concentration level to a higher level of iontophoretic current for increasing the concentration of the therapeutic agent in the body, said means for stepping up responsive to a control signal generated by a user activated timer; and
   the user-activated timer producing the control signal for a second predetermined interval in response to user activation.

9. The apparatus for introducing an ionized therapeutic agent into the body according to claim 6 wherein the means for driving the first level of iontophoretic current is a first and second battery, the first battery only supplying power for the predetermined interval, after which the means for driving the second level of iontophoretic current is the second battery which provides the power for maintaining the desired concentration level.

10. The apparatus for introducing an ionized therapeutic agent into the body according to claim 6 wherein the means for driving the first level of iontophoretic current is a first and second battery, the first battery mainly supplying power for the predetermined interval, after which the means for driving the second level of iontophoretic current is the second battery which mainly provides the power for maintaining the desired concentration level.

11. The apparatus for introducing an ionized therapeutic agent into the body according to claim 10 wherein the first battery depletes its energy supply during the predetermined interval so that at the end of the predetermined interval, it no longer supplies an appreciable amount of current.

12. The apparatus for introducing an ionized therapeutic agent into the body according to claim 6 wherein the means for driving the first level of iontophoretic current is a first and second constant current source, the first constant current source powered by a first battery and the second constant current source powered by a second battery, the first battery only supplying power to the first constant current source for the predetermined interval, after which the means for driving the second level of iontophoretic current is the second constant current source which provides the power for maintaining the desired concentration level.

13. The apparatus for introducing an ionized therapeutic agent into the body according to claim 6 wherein the means for driving the first level of iontophoretic current is a first and second constant current source, the first constant current source powered by a first battery and the second constant current source powered by a second battery, the first battery mainly supplying power to the first constant current source for the predetermined interval, after which the means for driving the second level of iontophoretic current is the second constant current source which mainly provides the power for maintaining the desired concentration level.

14. The apparatus for introducing an ionized therapeutic agent into the body according to claim 13 wherein the first battery depletes its energy supply during the predetermined interval so that at the end of the predetermined interval, it no longer supplies an appreciable amount of current.

15. The apparatus for introducing an ionized therapeutic agent into the body according to claim 6 wherein the means for driving the first and second levels of iontophoretic current comprises:
   a power source;
   a first plurality of constant current diodes for regulating current from the power source to a first output node;
   a second plurality of constant current diodes for regulating current from the power source to a second current output node;
   a plurality of switching means which may be selectively closed for selectively connecting selected ones of the first and second plurality of constant current diodes with the power source so that the first level of current can be programmed to be delivered to the first node and the second level of current can be programmed to be delivered to the second node; and
   a timed switch connecting the first and second nodes for the predetermined interval, after which time the second node is switched out.

16. The apparatus for introducing an ionized therapeutic agent into the body according to claim 15 wherein the selectively closed switching means are fused closed.

17. The apparatus for introducing an ionized therapeutic agent into the body according to claim 15 further comprising:
   a cover to the plurality of switching means with a plurality of holes, each hole associated with one of the plurality of switching means so that
   a stiletto may be selectively punched into the holes to selectively close the switching means.

18. The apparatus for introducing an ionized therapeutic agent into the body according to claim 6 wherein the means for driving the first and second levels of iontophoretic current comprises:
   a first iontophoretic current source for, with a control input for activation thereof, producing a first current;
   a second iontophoretic current source for producing a second current, the output of the first and second sources connected to the electrodes;
   a timer for producing an activation signal for the predetermined interval, the activation signal connected to the control input of the first iontophoretic current source;
   a power source applied to the first and second iontophoretic current sources;
   the first and second current sources active in response to the supplied power to produce in combination the first level of iontophoretic current while the activation signal is applied thereto; and
   whereby the first level of iontophoretic current is applied to the tissue by the first and second iontophoretic current sources when the first current source is active for the predetermined interval and the second, lower level of iontophoretic current is applied to the tissue by the second iontophoretic current source after the predetermined interval.

19. The apparatus for introducing an ionized therapeutic agent into the body according to claim 18 wherein the timer includes a user switch for activating the timer for a predetermined time, whereby the user is permitted to activate the first iontophoretic current source to increase the iontophoretic current level.

20. The apparatus for introducing an ionized therapeutic agent into the body according to claim 18 further comprising a deactivation timer means for deactivating the second iontophoretic current source for a predetermined deactivation period and for reactivating the second iontophoretic current source after the expiration of the predetermined deactivation period.

21. The apparatus for introducing an ionized therapeutic agent into the body according to claim 20 wherein the deactivation timer means deactivates the second iontophoretic current source after the predetermined interval.

22. Apparatus for introducing an uncharged therapeutic agent into the body, comprising:
   at least two electrodes;
   a drug reservoir for storing a liquid solvent containing the uncharged therapeutic agent;
   iontophoretic current generation means for:
      (i) driving a first level of iontophoretic current through said electrodes and the body tissue said electrodes are attached to, said first level applied for a predetermined interval; and
      (ii) driving a second, lower level of iontophoretic current through said electrodes and the associated body tissue beginning after said predetermined interval, said predetermined interval being timed so that the concentration of therapeutic agent in the body obtains approximately the desired concentration level during the predetermined interval and so that said second current level substantially maintains the desired concentration level thereafter.

* * * * *